United States Patent [19]
Drapeau et al.

[11] Patent Number: 4,682,010
[45] Date of Patent: Jul. 21, 1987

[54] IN-LINE ELECTRIC HEATER FOR AN AEROSOL DELIVERY SYSTEM

[75] Inventors: Donald F. Drapeau, Windsor; Benjamin N. Moore, Haddam; Henry B. Hall, Madison, all of Conn.

[73] Assignee: Safeway Products, Inc., Middletown, Conn.

[21] Appl. No.: 723,034

[22] Filed: Apr. 12, 1985

Related U.S. Application Data

[63] Continuation-in-part of Ser. No. 472,761, Mar. 7, 1983, abandoned.

[51] Int. Cl.$^4$ .................. H05B 3/00; F24H 3/00; A61M 16/00; H01C 3/00
[52] U.S. Cl. .................. 219/381; 128/203.27; 128/204.17; 138/128; 138/162; 219/307; 219/374; 219/375; 338/208
[58] Field of Search .............. 219/306, 307, 374, 375, 219/381, 382; 338/208; 138/128, 162; 128/203.26, 203.27, 204.17

[56] References Cited

U.S. PATENT DOCUMENTS

| | | | |
|---|---|---|---|
| 938,237 | 10/1909 | Hummelwell | 219/307 |
| 2,084,556 | 6/1937 | Hamilton | 338/208 |
| 2,759,092 | 8/1956 | Fortin | 338/208 X |
| 2,937,664 | 5/1960 | Plummer | 138/128 |
| 3,097,288 | 7/1963 | Dunlap | 219/307 |
| 3,099,737 | 7/1963 | Maxon | 219/307 |
| 3,344,257 | 9/1967 | Moeller | 219/374 |
| 3,425,456 | 2/1969 | Schibig | 138/162 |
| 4,147,923 | 4/1979 | Davis et al. | 219/381 X |
| 4,151,398 | 4/1979 | Maake | 219/374 |

FOREIGN PATENT DOCUMENTS

| | | | |
|---|---|---|---|
| 1174919 | 7/1964 | Fed. Rep. of Germany | 219/307 |
| 302281 | 10/1932 | Italy | 219/307 |
| 313229 | 5/1956 | Switzerland | 219/381 |

*Primary Examiner*—Anthony Bartis
*Attorney, Agent, or Firm*—Hayes & Reinsmith

[57] ABSTRACT

An in-line heater for an aerosol delivery system has an elongated tubular electrically insulated plastic body having first and second ends coaxially aligned along the major axis of the tubular body. The first and second ends contain an aerosol inlet and outlet, respectively. The plastic body has an unrestricted flow passage therein from the first to the second end and a self supporting electrically conductive spiral mesh heating element loosely fills the flow passageway within the body. The mesh heating element has a very low mass so as to be almost instantaneously responsive and extends across the space between the side walls of the flow passage to maximize the surface area thereof exposed to the aerosol mixture flowing through the passage. First and second terminals are adjacent the first and second housing ends, respectively, and are connected to the ends of the spiral mesh heating elements by a pair of crimped connector plates. Each terminal is disposed in a terminal housing having an internally serrated opening for securing a complementarily terminal sleeve having a serrated outer surface. The tubular plastic body may be formed from a pair of split tube halves. In an alternate embodiment, the tubular plastic body may be U-shaped with a water trap at the base.

11 Claims, 12 Drawing Figures

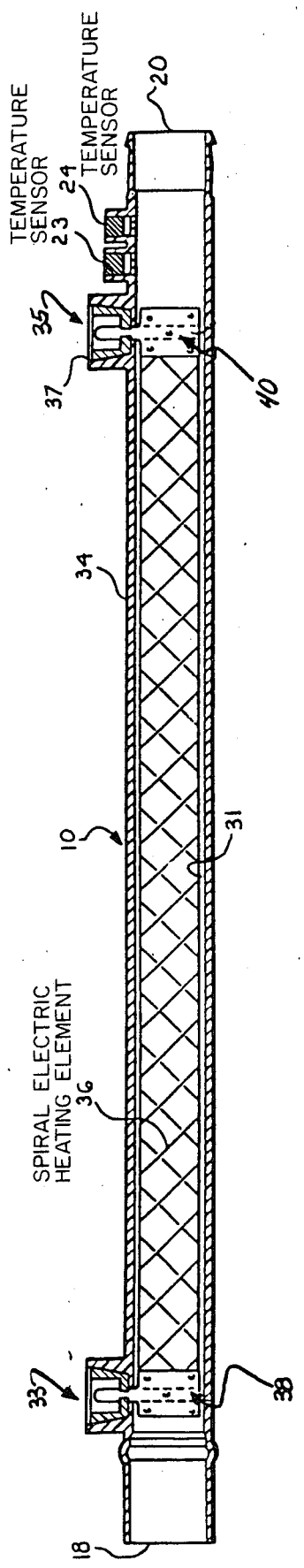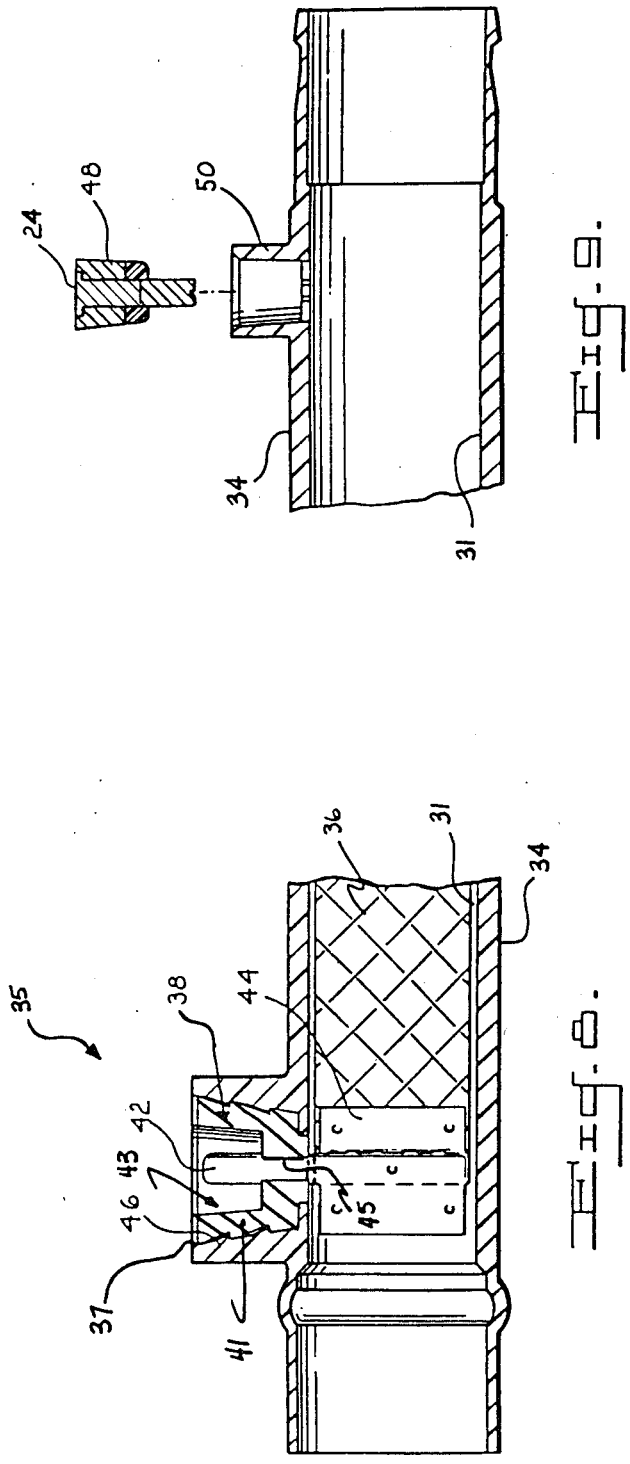

IN-LINE ELECTRIC HEATER FOR AN AEROSOL DELIVERY SYSTEM

BACKGROUND OF THE INVENTION

This is a continuation in-part application of U.S. patent application Ser. No. 472,761, filed Mar. 7, 1983, now abandoned.

This invention relates to the field of nebulizers or respirators or ventilators for patient care. More particularly, this invention relates to an in-line heater for a nebulizer, ventilator or respirator system. The in-line heater has an elongated air flow tube (preferably molded plastic) in which is positioned a spiral mesh heating element. The mesh heating element is connected to a pair of terminal leads at opposite ends of the tube to power the heater. The heater is a disposable unit, and it may contain one or more disposable thermostats or other temperature sensors. The in-line heater of this invention is disclosed and described in the environment of a nebulizer system having a disposable in-line heater, a water bottle heater and a coordinated controller for controlling moisture content and water droplet size as a function of the water outlet temperature and the aerosol temperature to the patient. It is to be understood that while the in-line heater is disclosed herein as disposable it is also contemplated that the in-line heater may also be reuseable (after apropriate sterilization).

Nebulizers are used to supply a humidified oxygen/air mixture (aerosol) to a patient to relieve respiratory congestion. The relative humidity, moisture content and droplet size of the water in the oxygen/air stream are extremely important factors for the proper operation of a nebulizer. Ventilators or respirators, on the other hand, are life support systems which are used to deliver an air/oxygen mixture to a patient at a comfortable temperature to sustain life.

A typical prior art nebulizer system in widespread use in hospitals and other patient care environments employs a 500 ml bottle of water which is positioned in a heating sleeve or heating chamber to be heated. Pressurized oxygen is directed at the water outlet from the bottle. The Bernoulli effect creates a low pressure boundary layer around an expanding oxygen jet to siphon water from the bottle. High energy oxygen flow shears off droplets at the bottle outlet creating humidification. Air is then mixed with the aerosol mixture of oxygen and water upstream of a baffle, whereby the larger droplets are removed from the air stream. The humidified gas stream is then delivered in the form of an aerosol to a patient. In this conventional prior art system, heating of the water is accomplished by a high mass heater which surrounds the entire water bottle. Heating of the water is accomplished by heating the bottle, per se, and then conducting heat from the heated bottle to the water contained therein. A time period of about 30 minutes is required for initially heating the water to operating temperature; and the only way to vary the temperature of the aerosol delivered to the patient is to (1) change the air flow rate, and (2) change the temperature of the entire contents of water and/or (3) change the oxygen/air mixture. Because of these requirements, the response time of this prior system is relatively high; and the control of the relative humidity, water droplet size and temperature are not as precise as would be desired. Additionally, burnout of the bottle itself was a prior art problem, because the bottle was directly contacted by the resistance heater, and the water could only be heated by first heating the bottle wall and then transferring the heat across the wall of the bottle of the water.

SUMMARY OF THE INVENTION

Many of these problems of the prior art are eliminated or reduced by the in-line heater apparatus of the present invention.

The in-line heater of the present invention will be described in the environment of a nebulizer system; but it will be understood it may be used in any system requiring a controllable heated air flow, especially for delivery to a patient. The heater is positioned in the aerosol supply line between the water supply and the patient. The heater control system includes control elements for sensing temperatures commensurate with the outlet from the water bottle and temperatures commensurate with the inlet or delivery to the patient. The difference between these temperatures is used to control moisture content and droplet size; and the actual temperature of aerosol delivery at the patient is also controlled. Moreover, the heater control system can separately sense and control the temperatures commensurate at in-line heater.

The present in-line heater and its associated tube may be disposable elements, thereby allowing a new heater and air tube to be employed for each patient, or may be formed of materials which are capable of withstanding sterilization processes for a reuseable unit. The heater can be located anywhere in the tube, but is preferably at the patient end for better control of moisture to the patient although safety requirements might dictate that it be at the bottle end of the tube. The temperature sensor at the patient may be in the delivery tube adjacent the end which goes to the patient, or it may be in the discharge end of the in-line heater.

The system is controlled by a electronic or electromechanical controller, such as a microprocessor, which has variable temperature settings, regulates the output of both the in-line heater and the water bottle heater or just the output of in-line heater separately and provides feedback (closed loop control) from the temperature sensor inputs.

The above-discussed and other advantages of the present invention will be apparent to and understood by those skilled in the art from the following detailed description and drawings.

BRIEF DESCRIPTION OF THE DRAWINGS

Referring now to the drawings, wherein like elements are numbered alike in the several FIGURES:

FIG. 7 is a sectional view, taken along line 7—7 of FIG. 2, of the in-line heater of this invention.

FIG. 8 partly in section and partly broken away, illustrates an end portion of the in-line heater of this invention.

FIG. 9 illustrates the mounting and positioning of a sensor in the in-line heater of this invention.

DESCRIPTION OF A PREFERRED EMBODIMENT

Figure 1:
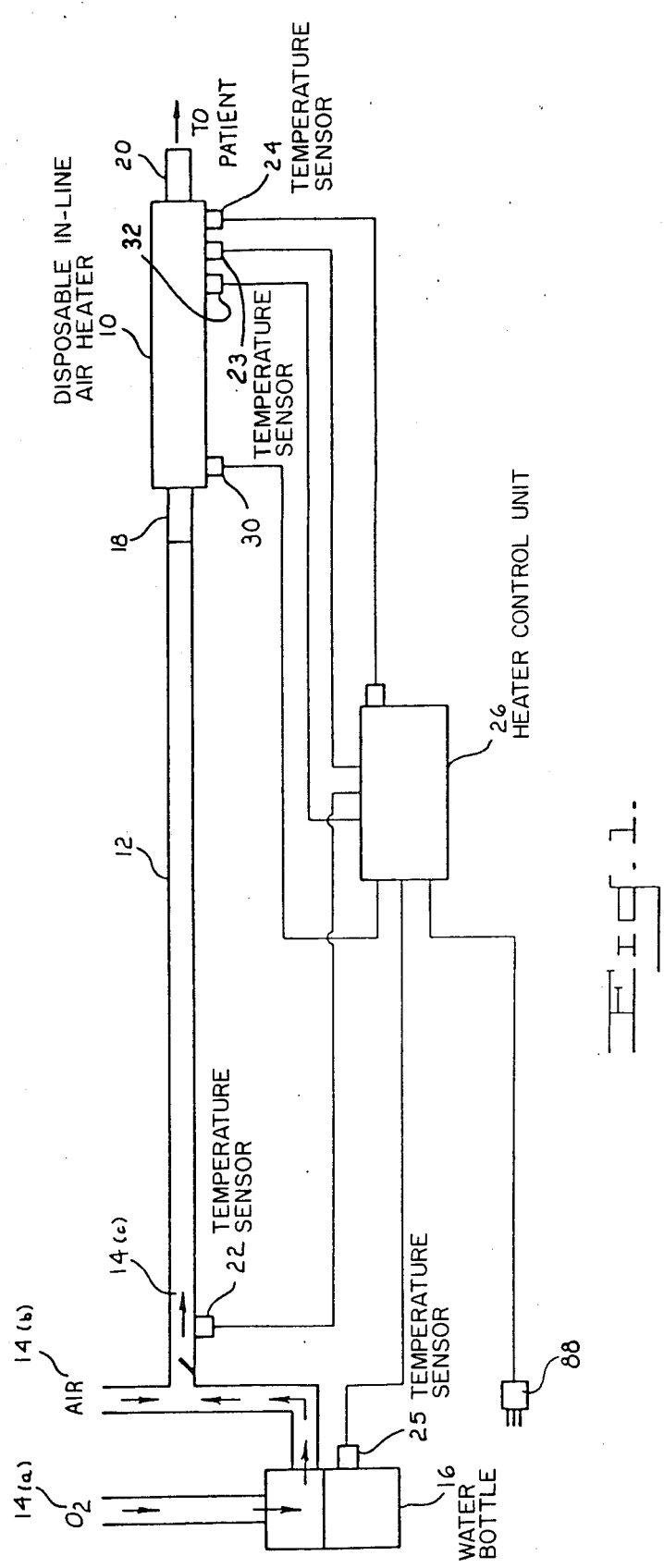
FIG. 1 shows a schematic of the nebulizer system with in-line heater of the present invention.

Referring to FIG. 1, an electric heater 10 is located in and forms part of an air line 12. A pressurized oxygen stream 14(a) is directed at the outlet from a water bottle 16. The Bernoulli effect creates a low pressure boundary layer around an expanding oxygen jet to draw water from the top of the bottle. The high energy oxygen stream shears off water droplets at the bottle exit to create humidification of the oxygen. Air 14(b) (usually unpressurized room air) is then mixed with the aerosol mixture of oxygen and water upstream of a baffle. The result is a humidified gas stream 14(c) of oxygen, air and water, which will sometimes be referred to as an aerosol. The aerosol mixture 14(c) is then delivered to the inlet 18 to heater 10. The humidified gas stream is then heated as may be required in heater 10, and it then flows from exit 20 of the heater through the remainder of air line 12 to a patient.

A temperature sensor 22 is positioned at the outlet of water bottle 16 and a temperature sensor 24 is positioned at the end of line 12 adjacent or immediately prior to the point at which the aerosol is delivered to the patient (or at the discharge end of heater 10 if heater 10 is at the end of line 12 immediately upstream of delivery to the patient). Temperature sensor 22 senses the outlet temperature of the aerosol from bottle 16, or a temperature commensurate therewith, while sensor 24 senses the temperature of the aerosol delivered to the patient, or a temperature commensurate therewith. Temperature sensors 22 and 24 are connected to control unit 26 which, in response to the temperature differential between sensors 24 and 22 will control the power to vary the output of heater 10 and the ouput of heat for the water bottle to provide the proper aerosol temperature, moisture content and droplet size jointly or aerosol temperature separately.

Also, overlimit temperature sensors 23 and 25 are located, respectively, at the outlet from heater 10 and in bottle 16. Temperature limit sensor 22 is a safety device which will, if the temperature at the exit of heater 10 has exceeded a design maximum, shut the system down. Similarly, temperature limit sensor 25 is also a safety device which will, if the temperature of bottle 16 exceeds design maximum, shut the system down. Overlimit sensors 23 and 25 are connected to controller 26 for coordinated operation as part of the controller system. Temperature sensors 23 and 24 may be, inexpensive and disposable sensors, such as thermocouples for the disposable in-line heater, as disclosed in more detail with regard to FIG. 9. Overtemperature sensors 23 and 25 are one shot fuse devices, which wil require service for resetting if they are tripped. They may be standard one shot fuse devices, or they may be the same as sensing devices 22 and 24, coupled with appropriate control electronic to be normally closed switches which trip open upon reaching an upper temperature limit and stay open until reset. Power lines having terminal connectors 30 and 32 extend from control unit 26 for connection to the heater element to power the heater.

Figure 2:
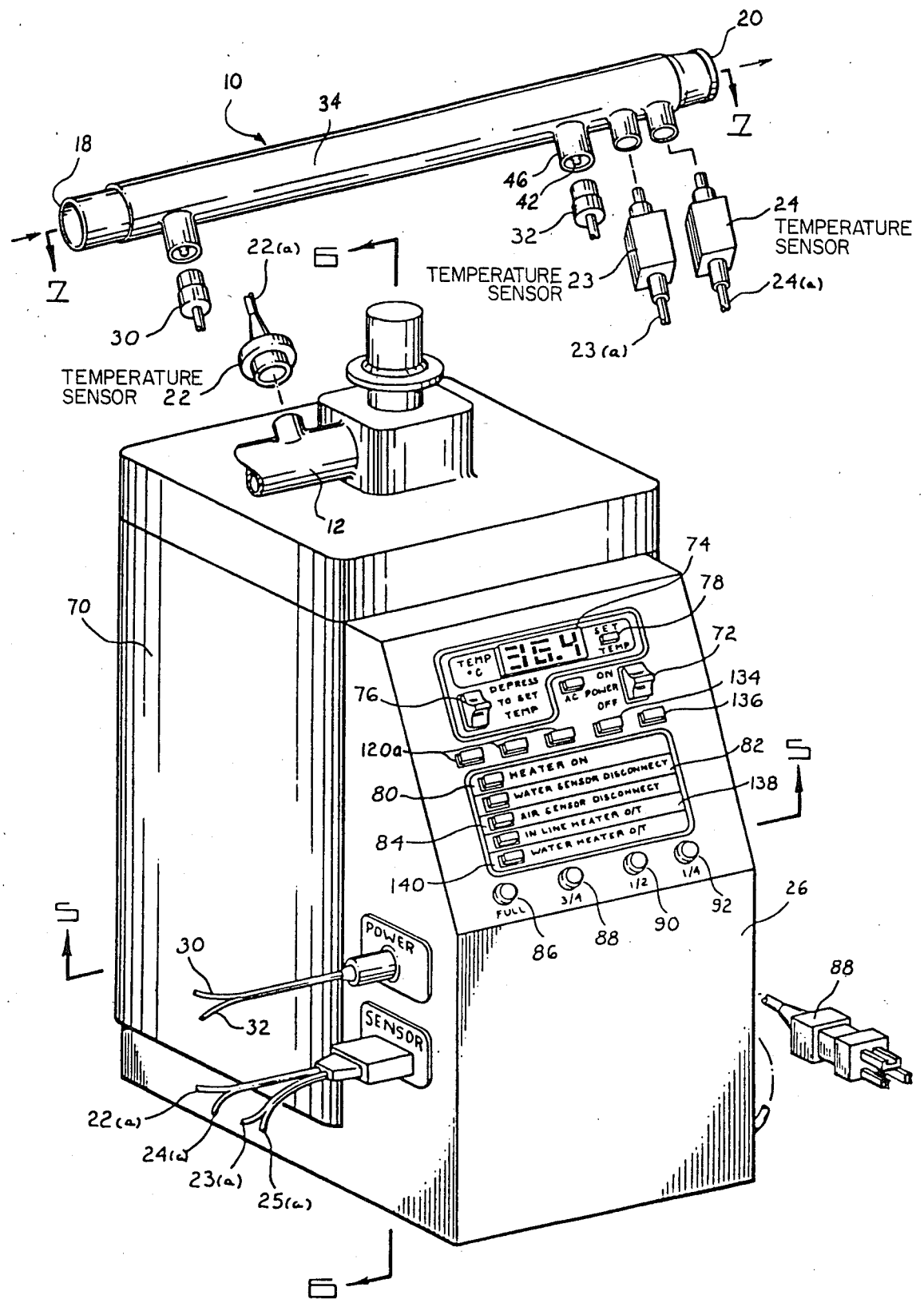
FIG. 2 is a partial detailed view of the system of FIG. 1 showing more details of the in-line heater of the present invention and the controller.

Referring now to FIGS. 7–11, the details of the in-line heater 10 (and alternative embodiments) of this invention are shown. Heater 10 is preferably formed of molded plastic tube 34 having an elongated passage 31 formed therein. The inlet to the tube is indicated at 18, and axially aligned therewith along major axis of tube 34 is outlet to tube, indicated at 20. Adjacent each ends of tube 34 are housings 33, 35, positioned preferable perpendicular to axis of tube. Within tube 34 is located an elongated spiral metallic mesh heating element 36 secured at its ends to terminals 38, 40, which, in turn, are connectable to power line terminals connector 30 and 32, (see FIG. 2) respectively. The mesh heating element 36 extends axially within tube and is wound spirally within tube so as to loosely fill the tube from one of the tube ends to the other and substantially entirely across the space between sidewalls of tube so that the maximum surface area of mesh is exposed to the aerosol mixture passing within tube. With the in-line heater so designed, impedence and restriction of the low pressure aerosol flow through passage 31 of tube is minimized allowing substantially uninterrupted aerosol flow. Also, with this design substantially all of aerosol mixture passes through the interwoven mesh heating element 36. The mesh heating element may, for example, be formed from thin expanded wire which is coated with a material suitable to resist corrosion. Moreover the mesh provides the desired electrical resistance heater when connected a suitable power source. The mesh heating element 36 forms a plurality of series-parallel electrical circuits, so that heat transfer is not lost if one or more of the strands of mesh should break or otherwise fail. The mesh heating element 36 has a very low mass which enables mesh to be self supporting within tube except at its ends and to respond almost instantaneously to changes in electrical power at terminals 38, 40 thereby providing essentially instantaneous temperature regulation of the aerosol mixture.

Each terminal 33, 35 is connected to one of power supply terminal connectors 30, 32 of control unit 26. Terminals 33, 35 are positioned in opening 37 of terminal housing 46; the opening 37 being internally serrated, as shown in FIG. 8, to receive and fix in place a terminal sleeve 41 having a serrated outer surface. Walls of sleeve 41 form bore 43 in which rounded-tip post 42 protrudes upwardly through aperture 45 in base of sleeve 41 from metal electrode or connector 44. Metal electrode 44 may be formed of plates which are positioned within tube 34 in a narrow profile to enable free inlet and outlet flow of aerosol and to minimize impedence of aerosol flow at tube ends.

Referring now to FIG. 8, details of terminal 38 are shown; and it will be understood that the detail of terminal 40 is identical to that shown and described in FIG. 8. Terminal 38 contains an elongated, rounded-tip post 42 which extends upwardly from interior of tube from a pair of connector plates 44 (only one of which is shown). Mesh 36 is positioned between the two plates 44, and the plates are fixed together, by such means as crimping, to lock the mesh between the plates. The internally recessed bore 43 of sleeve 41 is formed so that a reciprocally shaped power line connector 30 and 32 of control unit 26 can be readily connected and disconnected.

The aerosol mixture enters the heater at inlet 18 and flows through the center of tube 10 where it is in intimate contact with the spirally wound mesh heating element 36. The aerosol mixture then leaves the heater under low pressure at exit end 20 for delivery to the patient. As previously noted, thermocouple temperature sensors 22 and 24 monitor the temperature differential in the aerosol between the water bottle exit and the patient. These temperature signals are fed to control unit 26 where they are used to control the power supplied to mesh heating element 36 to control aerosol temperature, moisture content and droplet size, as will be more fully explained hereinafter.

Referring to FIG. 9, another detail is shown with regard to the mounting and positioning of one of the sensors (e.g., sensor 24), such as a thermocouple or solid state sensor, and it will be understood that the mounting of the other temperature sensors is essentially identical whether in heater 10, line 12 or in the housing for water bottle 16. Sensor 24 is a chromel/constantan unit (or other suitable thermocouple material combination) housed in a plastic plug 48 which in turn, is engaged by a friction fit in a housing 50 on the exit to heater tube 34.

Referring now to FIGS. 10A and 10B, two alternative configurations are shown for plastic tube 34. As shown in FIG. 10A plastic tube 34 may be in the form of a pair of split tube halves 52 and 54 which may be joined together to form the final tube unit. In the embodiment of FIG. 10B, the two tube halves are joined together by a flexible hinge 56. Either of the configurations of FIG. 10A or 10B may be employed to facilitate mounting of the mesh heating element 36; or the mesh heating element 36 may, if desired, be mounted in a one piece tube.

Referring now to FIG. 11, an alternative configuration for the heater tube is shown. In the FIG. 11 embodiment, heater tube 10' is in the form of a U-shaped element 58 of circular cross-section, with heater mesh 36 spirally wound from one end of the U-shaped element to the other in the hollow interior of tube 58. This U-shaped tube may be of particular utility in that it may be provided with a water trap 60 at the bottom of the bridge between the legs of the U-shaped element. Water trap 60 may be used to conveniently and simply collect and remove excess water from the system.

All of the disclosed metal objects of the in-line heater are preferably coated with a plastic material that has the requisite heat, insulating heat resistant and oxidizing resistance properties.

Referring now to FIGS. 2, 5 and 6, exterior view of the combined controller and bottle warmer unit (FIG. 2) is shown and details of the bottle water unit are shown (FIGS. 5 and 6).

Referring first to FIG. 2, control unit 26 is joined or otherwise connected to a housing 70 which houses water bottle 16. The exterior of temperature controller 26 has an on/off power switch 72, a digital temperature indicator 74, a temperature set or select button 76, a temperature set interlock 78 (which must be depressed before the temperature select button 76 can be operated to change temperature selection), a series of lights 80, 82 and 84 to indicate, respectively, when heater 10 is powered, when bottle temperature sensor 22 has been disconnected from the system and when patient delivery temperature sensor 24 has been disconnected from the system. The face of controller 26 also includes a series of lights 86–92 to indicate, respectively, the level of water in bottle 16 at the levels of full, three quarters, one half and one quarter. Power leads 30 and 32 run from controller 26 to the power terminals of heater 10; lines 22*a* and 24*a* connect temperature sensors 22 and 24, respectively, to controller 26; and lines 23*a* and 25*a* connect overlimit temperature sensors 23 and 25, respectively, to controller 26. A grounded power supply cord 88 is provided to deliver power to the unit.

Referring to FIGS. 5 and 6, the details of a water bottle heater component of the system are shown. The bottle heater has a housing 70 which contains central water bottle chamber 89 and a plurality of elongated and semi-cylindrical recesses 90. Water bottle 16 is positioned in chamber 89, and each recess 90 houses an infrared bulb 92 which is screw fitted into a negative terminal socket 94 in housing base 96. A positive terminal plate 98 on the bottom of base 96 also contacts each bulb to complete the power supply circuit to the bulbs. This power supply circuit may be internally connected between housing 70 and the power supply of control 26. The wall of each recess 90 may be lined with aluminum or another reflector material 100 to reflect and focus infrared energy into the water bottle 16.

Infrared bulbs 92 surround bottle 16. Bulbs 92 and their corresponding reflectors 100 in each recess deliver and focus infrared energy to the contents of bottle 16 to heat the water rapidly and efficiently and with much faster response time than was possible with the prior art resistance type nebulizer bottle heaters. The infrared bottle heater and the details of its construction disclosed herein also offer significant advantages over the prior art in that bottle casing or wall temperature is reduced and bottle burnout is eliminated or reduced. Response time for heating the water is reduced significantly because the infrared rays from bulbs 92 penetrate or pass through the shell of bottle 16 to directly heat the water in the bottle. Also, since the heater elements (bulbs 92) are not directly in contact with the bottle, and because the shell of the bottle is not heated in transfer heat to the water, bottle burnout is eliminated or reduced.

A water level sensor system 95 (see FIG. 3) consists of a series of light sources 97 and corresponding light receivers 99 in housing 70. The light emitters and receivers are each arranged in vertical arrays at locations corresponding to water levels (e.g., full, $\frac{3}{4}$, $\frac{1}{2}$, $\frac{1}{4}$). Light emitted from an emitter 97 will be scattered by the water and not received at its corresponding receiver 99 if the water level in the bottle is higher than that emitter and receiver pair. If the water level is below the height of a receiver-emitted pair, the light from the emitter 97 will be received at the receiver 99 to indicate the water level which will then be displayed on display lights 86–92 of controller 26. Inverter circuitry may be used to connect light receivers 99 to the respective display lights 86–92 whereby all four lights will be on when the bottle is full, and each light will go out as its level is passed. Other water level sensors could be used, such as a pressure sensor at the bottom of chamber 89.

Turning now to a consideration of FIG. 3, a block schematic of the control system for a nebulizer system incorporating temperature and moisture control is shown. The block schematic of FIG. 3 includes both the control unit 26 and various external sensors and components previously described; and it will be understood that the showing in FIG. 3 is intended to be only a block diagram form to show the interrelationship and functioning of the various parts. As shown in FIG. 3, the control unit 26 includes, as a principle component, a microprocessor 100 for carrying out appropriate logic functions. It will be understood, of course, that microprocessor 100 will be programmed in accordance with any suitable state of the art programming to accomplish the logic control functions to be discussed hereinafter.

Figure 3:
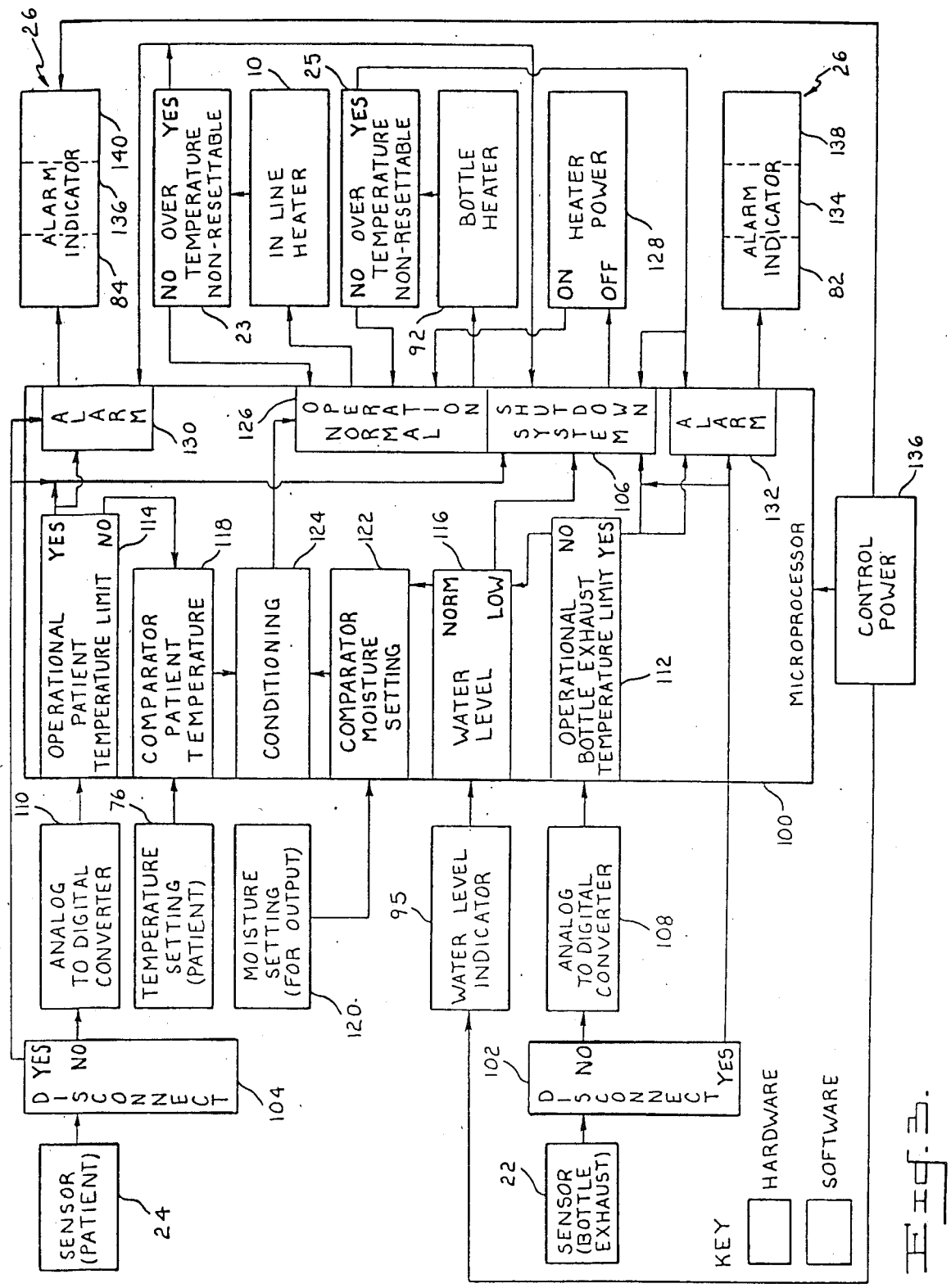
FIG. 3 shows a block diagram of a first version of a microprocessor control.

Assuming that the system of FIG. 3 has been set and is operating to deliver an aerosol at an appropriate temperature and moisture content to a patient, a sequence of operation through the block diagram of FIG. 3 will now be described. The temperature of the aerosol being delivered to the patient is sensed at patient delivery temperature sensor 24, and the temperature of the aerosol exiting from the water supply bottle is sensed at bottle exhaust temperature sensor 22. Each of these temperature sensors generates a signal, such as in the millivolt range, commensurate with and proportional to the temperature being sensed. Each of sensors 22 and 24 includes an interface disconnect 102 and 104, respectively, which is incorporated in the system to insure that each of the sensors is properly connected before operation of the control system is allowed to proceed. If either of these disconnect interfaces determines that there is an incomplete hardware connection of its associated sensor, a "YES" software signal will be generated and delivered to the system shutdown section 106 of microprocessor 100 to shut the system down. The delivery of this signal from either disconnected interface to system shutdown section 106 will, in turn, result in a generation of an "OFF" instruction to heater power unit 128 to disconnect the power to both heater 10 and the infrared heater bulbs 92 for bottle 16. Also, a signal will be delivered to activate audio alarm 130 and visual alarm 84 if sensor 24 is disconnected; and a signal will be delivered to activate audio alarm 132 and visual alarm 82 if sensor 22 is disconnected. Assuming that the disconnect interfaces 102 and 104 show that the sensors are properly connected (i.e., there is no disconnect), "NO" software signals are generated to pass the outputs from the sensors 22 and 24 to the analogue/digital convertors (ADC) 108 and 110 which are under software control to accept the signals from the sensors. The signal from ADC 108 is then delivered to microprocessor section 112 which is programmed or set for an operational water bottle exit temperature limit which has been preselected. This operational water bottle exit temperature limit is selected to be the maximum water bottle exit temperature to be permitted during normal functioning of the system. The temperature selection for the water bottle exit is actually determined by and as a function of moisture level desired in the aerosol. Moisture level selector system 120 (which includes an array of moisture setting or selection buttons 120 (a) on control 26) establishes the bottle exit or exhaust temperature to achieve a desired moisture content for the aerosol. If microprocessor unit 112 determines that the actual bottle discharge temperature called for by the moisture control system equals or exceeds the preselected maximum value for normal system operation, a "YES" signal will be generated and delivered to system shutdown unit 106 to shutdown the heater power unit 128 and automatically reset the unit to recycle for normal operation when the over temperature condition has been cleared. Similarly, the output from ADC converter 110 is delivered to operational patient temperature limit unit 114 which is programmed or set for a predetermined maximum aerosol delivery temperature to the patient during normal operation. The setting of temperature selector 76 is the targeted temperature for delivery to the patient. If microprocessor unit 114 determines that the actual patient delivery temperature sensed by sensor 24 equals or exceeds the preselected patient temperature limit (which may, for example, be caused by temporary overheating of the aerosol from the two heat sources), then a "YES" signal wil be generated at microprocessor unit 114 delivered to system shutdown unit 106 to shutdown the output power and automatically reset the unit to normal operation when this overtemperature condition has been cleared. In the event of a "YES" output from either unit 112 or 114, audio and visual alarm indications will also be initiated to indicate the respective condition.

Assuming that "NO" signals are generated at units 112 and 114 (commensurate with an indication that the respective temperature limits have not been exceeded), unit 112 will deliver a program signal to microprocessor water level unit 116 and a program signal from unit 114 is directed to patient temperature comparator unit 118.

A "NO" output will be generated from the units 112 and 114 in the event the temperature information being fed to those units does not exceed the preset limit for each unit. In that event, the information from bottle temperature sensor 22 will be delivered to a water level sensing unit 116, and the information from sensor 24 will be delivered to patient temperature comparator unit 118. Water level unit 116 receives the information from unit 112 and permits that information to be passed for further operation if the water level in the bottle (as determined by water level sensing system 95) is within acceptable limits. If the water level is low, a signal is passed to system shutdown unit 106 to shutdown output power and automatically reset to normal operation when the water level condition has been cleared. If the water level is within normal limits, then the information delivered to unit 116 will be passed for further operation. As previously described, water level indicators 86–92 are associated with water level sensor 95 and unit 116 to provide visual indication of the water level.

Temperature set unit 76 delivers an input signal to patient temperature comparator unit 118 where the selected temperature is compared with the actual temperature information delivered to comparator 118 from unit 114. A desired moisture setting is selected at moisture selector system 120 (which includes the several selectors 120 (a); and a signal commensurate therewith is delivered to moisture comparator unit 122 which, in turn, receives the information from bottle sensor 22 via microprocessor units 112 and 116. The bottle temperature exhaust information from sensor 22 is adjusted at moisture setting comparator 122 according to the moisture selection setting information from unit 120 to either increase or decrease the amount of moisture to the patient. The information from temperature comparator 118 and moisture comparator 122 passes to conditioning unit 124. Conditioning unit 124 acquires the software information from the patient temperature comparator and the moisture setting comparator, interprets that information and develops signals for delivery to normal operation unit 126 to establish the proper temperature and moisture levels for delivery to the patient.

Normal operation unit 126 generates software informational signals to control the operation of in-line heater 10 and bottle heater infrared bulbs 92 to increase or decrease power to these units. A heater power source 128 is connected to normal operation unit 126 to deliver power to unit 126 which, in turn, controls the power levels delivered to in-line heater 10 and bottle heater bulbs 92. The increase or decrease of power delivered to in-line heater 10 and bulbs 92 is effective to establish the temperature and moisture settings called for in the unit. Moisture delivery (humidity level and water droplet size) is controlled by establishing a desired temperature differential between patient delivery sensor 24 and bottle exhaust sensor 22 through the adjustment of power to the in-line heater 10 and bottle heaters bulbs 92.

As previously indicated, the system shutdown unit 106 will operate to shut off power in the event certain conditions occur. The recapitulate these conditions, if a "YES" signal is generated at disconnect 102, shutdown signals will be delivered to units 106 which will, in turn, deliver a signal to turn off the heater power unit 128, and activate both audio alarm 132 and visual alarm 82. Similarly, if a "YES" signal is developed at disconnect 104, a shutdown signal will be delivered to unit 106 which will, in turn, disconnect the heater power 128 and activate an audio alarm 130 and visual alarm 84. If a "YES" signal is generated at unit 112 or unit 114, system shutdown signals will be delivered to unit 106, which will cause temporary disconnect of output power 128 and actuation of audio alarms 130 and 132 and visual alarms 134 and 136. If a "low" signal is generated at water level unit 116, a shutdown signal will be delivered to system shutdown unit 106 which will, in turn, disconnect output power 128 until the water level in the bottle is returned to an acceptable level and activate the audio and visual alarm.

The system of FIG. 3 also incorporates overtemperature limit sensors 23 and 25. As previously described, sensor 23 senses the aerosol temperature discharged from in-line heater 10, and sensor 25 senses the temperature of the water in bottle 16. Sensors 23 and 25 are, in effect, one shot units or fuses (either hardware fuses or thermostats coupled with electronics to constitute one shot fuse elements). Sensor 23 is set for a maximum temperature higher than operational patient temperature limit 114; and sensor 25 is set for a maximum temperature higher than operational water temperature limit 112. As long as the temperature sensed by either of these sensors does not exceed the predetermined maximum limit for its respective unit, the output from each of these sensors will be, in effect a "NO" signal which is delivered to the normal operation unit 126 and permits normal functioning of the unit. However, if either of these units generates a "YES" indicating that the temperature limit has been exceeded, the "YES" signal will be delivered to system shutdown unit 106 to disconnect output power at 128. Also, signals will be delivered to activate the associated audio alarm 130 or 132 and the associated visual alarm 138 or 140. Sensor elements 23 and 25 are, as indicated above, fuse type elements and they are one shot units. Once a unit has been activated to generate a "YES" signal, automatic reset will not take place. The unit, i.e., fuse must be reset, preferably by factory maintenance so that the source of the trouble which caused the unit to cease operation can be determined and corrected. Any appropriate temperature responsive overlimit type element can be used for sensors 23 and 25.

As indicated in the drawing of FIG. 3, control power from unit 136 is delivered to all control elements and all alarm elements to provide proper voltage and current for operation of these elements. Also, it will be noted that audio alarms 130 and 132 are schematically shown and described as responding to several input signals; but separate audio alarms may be used. Similarly, visual alarms 82, 134 and 138 are shown schematically as subsections of one unit and visual alarms 84, 136 and 140 are shown as subsections of another unit. However, in actual practice, separate visual alarm components may be employed for each warning light.

In accordance with the present invention, an improved nebulizer may also be realized with a subsystem which omits in-line heater 10 and the moisture control feature previously described. This subsystem omits in-line heater 10, water bottle exhaust temperature sensor 22 and the moisture setting and control features. This subsystem retains patient delivery temperature sensor 24 (which could be located at the patient delivery end of tube 12) and water bottle overtemperature sensor 25 and all other components of the system previously described.

Turning now to a consideration of FIG. 4, a block schematic of the control system for this nebulizer subsystem omitting the in-line heater and moisture control is shown, with prime (') superscripts for elements corresponding to the FIG. 3 diagram. The block schematic of FIG. 4 includes both the control unit 26' and various external sensors and components for this nebulizer subsystem; and it will be understood that the showing in FIG. 4 is intended to be only a block diagram form to show the interrelationship and functioning of the various parts. As shown in FIG. 4, the control unit 26' includes, as a principle component, a microprocessor 100' for carrying out appropriate logic functions. It will be understood, of course, that microprocessor 100' will be programmed in accordance with any suitable state of the art programming to accomplish the logic control functions to be discussed hereinafter.

Assuming that the system of FIG. 4 has been set and is operating to deliver an aerosol at an appropriate temperature to a patient, a sequence of operation through the block diagram of FIG. 4 will now be described. The temperature of the aerosol being delivered to the patient is sensed at patient delivery temperature sensor 24', along with the temperature of the aerosol. This temperature sensor generates a signal commensurate with and proportional to the temperature being sensed. Sensor 24' includes an interface disconnect 104' which is incorporated in the system to insure that the sensor is properly connected before operation of the control system is allowed to proceed. If the disconnect interface determines that there is an incomplete hardware connection of the patient delivery sensor, a "YES" software signal will be generated and delivered to the system shutdown section 106' of microprocessor 100' to shut the system down. The delivery of this signal from disconnect interface 104' to system shutdown section 106' will, in turn, result in a generation of an "OFF" instruction to heater power unit 128' to disconnect the power to the infrared heater bulbs 92' for bottle 16'. Also, a signal will be delivered to activate audio alarm 130' and visual alarm 84' if sensor 24' is disconnected. Assuming that the disconnect interface 104' shows that the patient delivery temperature sensor 24' is properly connected (i.e., there is no disconnect), a "NO" software signal is generated to pass the output from the sensor 24' to the analogue/-digital convertor (ADC) 110' which is under software control to accept the signal from sensor 24'. The output from ADC convertor 110' is delivered to operational patient temperature limit unit 114' which is programmed and set for a predetermined maximum aerosol delivery temperature to the patient during normal operation. The setting of temperature selector 76' is the targeted temperature for delivery to the patient. If microprocessor unit 114' determines that the actual patient delivery temperature sensed by sensor 24' equals or exceeds the preselected patient temperature limit (which may, for example, be caused by temporary overheating of the aerosol from the two water bottle heater), then a "YES" signal will be generated at microprocessor unit 114' and delivered to system shutdown unit 106' to shutdown the output power and automatically reset the unit to normal operation when this overtemperature condition has been cleared. In the event of a "YES" output from unit 114', audio and visual alarm indications will also be initiated to indicate the respective condition.

Assuming that "NO" signals are generated at unit 114' (commensurate with an indication that the operational patient temperature limit has not been exceeded), a program signal from unit 114' is directed to patient temperature comparator and conditioning unit 118'.

A "NO" output will be generated from the unit 114' in the event the temperature information being fed to that unit does not exceed the preset limit for unit 114'. In that event, the information from sensor 24' will be delivered to the patient temperature comparator and conditioning unit 118'.

Temperature set unit 76' delivers an input signal to patient temperature comparator and conditioning unit 118' where the selected temperature is compared with the actual temperature information delivered to comparator 118' from 114'. Unit 118' compares and interprets the two inputs and develops output signals for delivery to normal operation unit 126'; to establish the proper temperature for delivery to the patient. The output from unit 118' is delivered to water level unit 116'. Water level unit 116' receives the information from unit 114' and permits that information to be passed for further operation if the water level in the bottle (as determined bywater level sensing system 95') is within acceptable limits. If the water level is low, a signal is passed to system shutdown unit 106' to shutdown output power and automatically reset to normal operation when the water level condition has been cleared. If the water level is within normal limits, then the information delivered to unit 116' will be passed to normal operation unit 126' for further operation. As previously described, water level indicators 86'-92' are associated with water level sensor 95' and unit 116' to provide visual indication of the water level.

Normal operation unit 126' generates software informational signals to control the operation of bottle heater infrared bulbs 92' to increase or decrease power to these units. A heater power source 128' is connected to normal operating unit 126' to deliver power to unit 126' which, in turn, controls the power levels delivered to bottle heater bulbs 92'. The increase or decrease of power delivered to bulbs 92' is effective to establish the aerosol temperature settings called for in the unit.

As previously indicated, the system shutdown unit 106' will operate to shut off power in the event certain conditions occur. To recapitulate these conditions, if a "YES" signal is generated at disconnect 104', a shutdown signal will be delivered to unit 106' which will, in turn, disconnect the heater power 128' and activate and audio alarm 130' and visual alarm 84'. If a "YES" signal is generated at unit 114', a system shutdown signal will be delivered to unit 106', which will cause temporary disconnect of output power 128'. If a "low" signal is generated at water level unit 116', a shutdown signal will be delivered to system shutdown unit 106' which will, in turn, disconnect output power 128' until the water level in the bottle is returned to an acceptable level and activate the audio and visual alarms.

Figure 4:
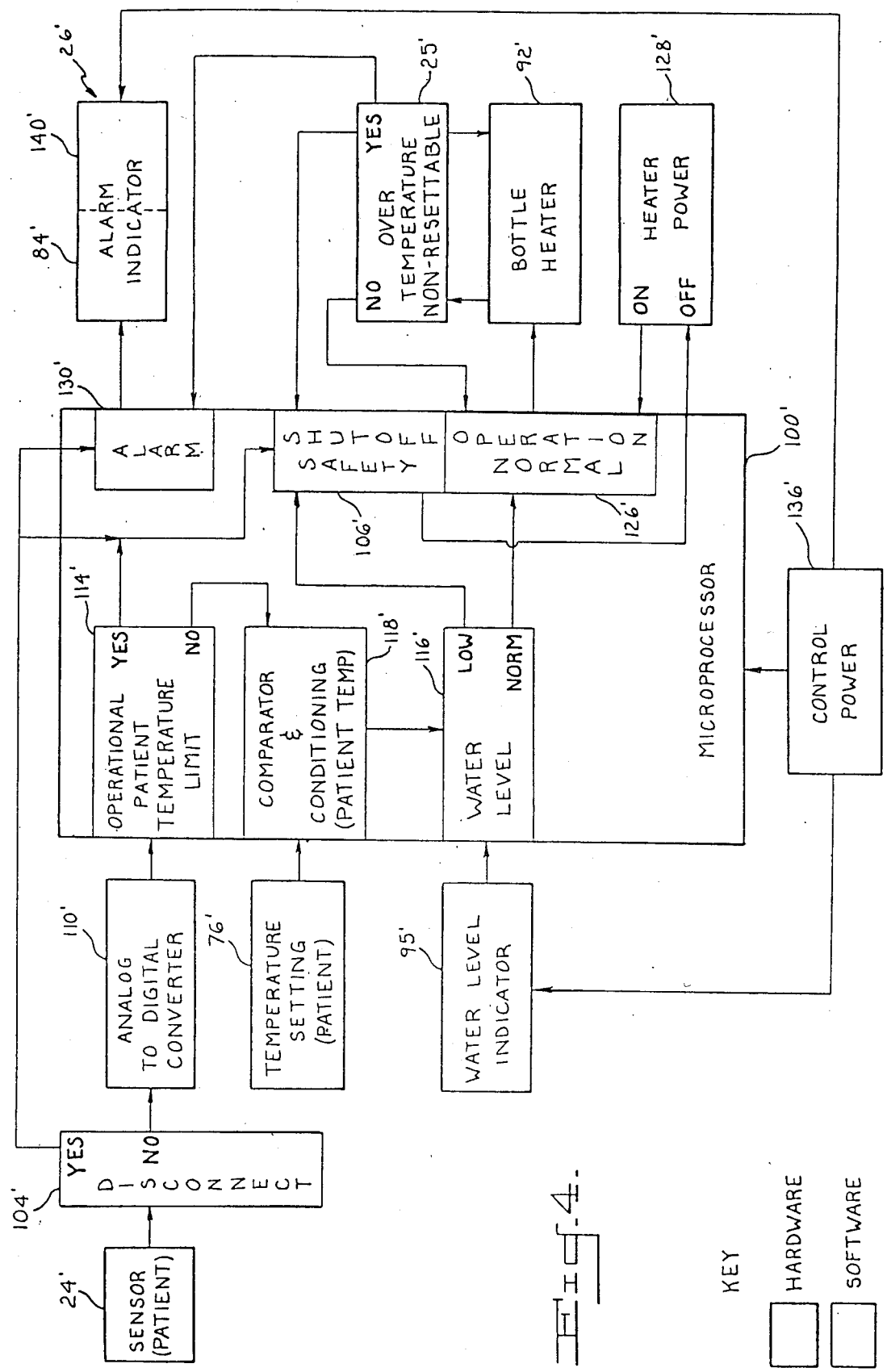
FIG. 4 shows a block diagram of a second version of a microprocessor control.
Figure 5:
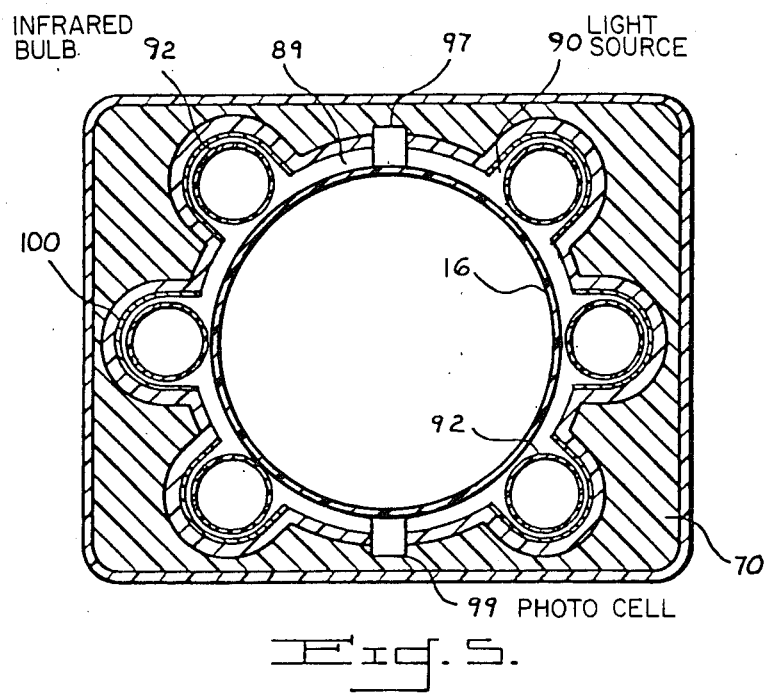
FIG. 5 shows a view, along line 5—5 of FIG. 2, of details of the water bottle heater.
Figure 6:
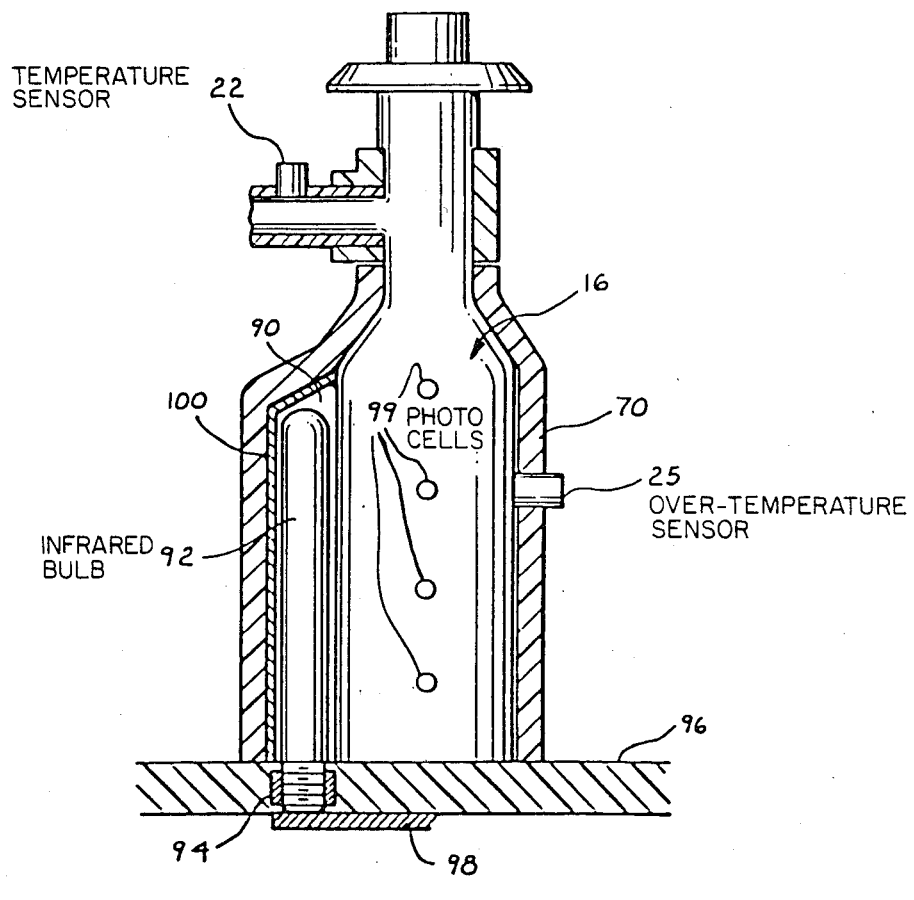
FIG. 6 shows a view, along line 6—6 of FIG. 2, of details of the water bottle heater.
Figure 11:
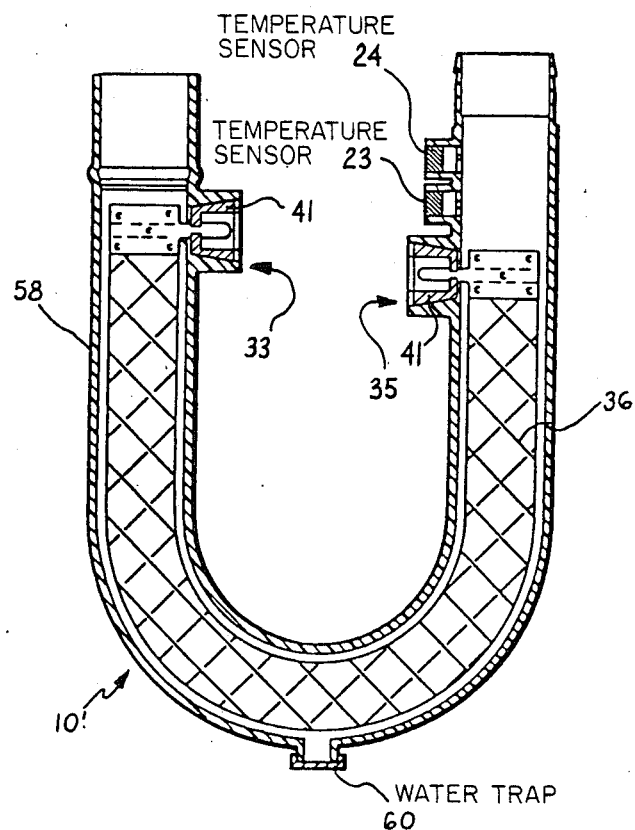
FIG. 11 shows another modified version of an in-line heater in accordance with the present invention.
Figure 10A:
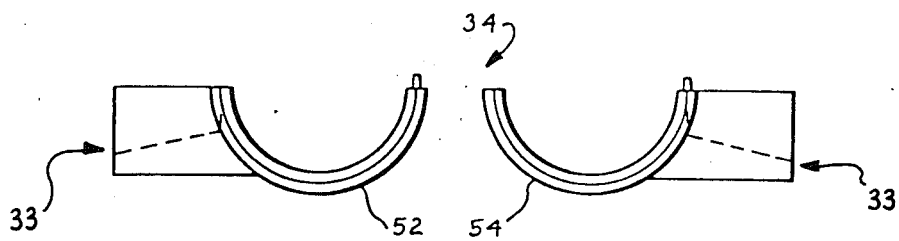
FIG. 10A illustrates a configuration of the plastic tube of the in-line heater.
Figure 10B:
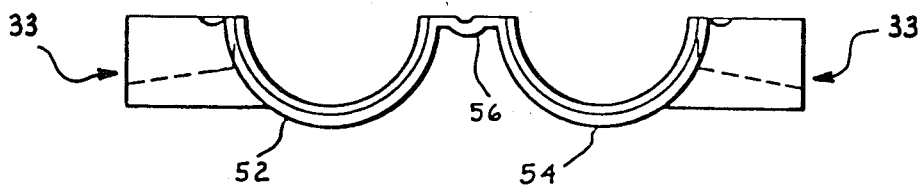
FIG. 10B is an alternate embodiment of a configuration for the plastic tube of the in-line heater of this invention.

The system of FIG. 4 also incorporates water bottle overtemperature limit sensor 25'. As previously described, sensor 25' senses the absolute temperature of the water in bottle 16'. Sensor 25' is, in effect, a one shot unit or fuse (either hardware fuse or thermostat coupled with electronics to constitute a one shot fuse element). As long as the temperature sensed by sensor 25' does not exceed its predetermined maximum limit, the output from sensor 25' will be, in effect, a "NO" signal which is delivered to the normal operation unit 126' and permits normal functioning of the unit. However, if sensor 25' generates a "YES" indicating that the water bottle temperature limit has been exceeded, the "YES" signal will be delivered to system shutdown unit 106' to disconnect output power at 128'. Also, a signal will be delivered to activate the audio alarm 130' and the associated visual alarm 140'. Sensor element 25' is as indicated above, a fuse type element and it is a one shot unit. Once sensor 25' has been activated to generate a "YES" signal automatic reset will not take place. The unit, i.e., fuse must be reset, preferably by factory maintenance so that the source of the trouble which caused the unit to cease operation can be determined and corrected. Any appropriate temperature responsive over limit type element can be used for sensor 25'.

As indicated in the drawing of FIG. 4, control power from unit 136' is delivered to all control elements and all alarm elements to provide proper voltage and current for operation of these elements. Also it will be noted that audio alarm 130' is schematically shown and described as responding to several input signals; but separate audio alarms may be used. Similarly, visual alarms 84' and 140' are shown as subsections of a single unit. However, in actual practice, separate visual alarm components may be employed for each warning light.

It should also be noted that the improved infrared water bottle heater and/or the improved in-line heater, and/or the moisture and droplet size control features hereof may be used separately or together in ventilator or respirator systems.

While preferred embodiments have been shown and described, various modifications and substitutions may be made thereto without departing from the spirit and scope of the invention. Accordingly, it is to be understood that the present invention has been described by way of illustrations and not limitation.

We claim:

1. An in-line heater for an aerosol delivery system comprising:

an elongated tubular electrically insulated body having first and second ends coaxially aligned along the major axis of said tubular body, said first and second ends containing an aerosol inlet and outlet, respectively, said body further having an unrestricted flow passage therein from the first to the second end, and first and second terminal housings adjacent said first and second ends thereof;

a first electrical terminal positioned in the first terminal housing of said tubular body;

a second electrical terminal positioned in the second terminal housing of said tubular body; and heating means connected to said first and second terminals, said heating means comprising an elongated strip of electrically conductive mesh of very low mass so as to be almost instantaneously responsive and self supporting, the conductive mesh strip axially extending and being spirally wound within the tubular body to loosely fill the tubular body from its first end to its second end and to extend substantially across the space between the sidewalls of the tubular body so that the maximum surface area of the mesh strip heating means is exposed to the aerosol mixture passing through the tubular body thereby minimizing the impedance, interruption and restriction of the aerosol flow.

2. The in-line heater of claim 1 wherein:
the unrestricted flow passage is substantially straight.

3. The in-line heater of claim 1 wherein:
said mesh heating element comprises a plurality of series-parallel electrical circuits to produce a uniform temperature distribution in an aerosol as the aerosol passes through the tubular body.

4. The in-line heater of claim 1 wherein:
each of said terminals has a narrow profile to minimize restriction of aerosol flow in tubular body and is formed to enable ready interconnection with a power source, the terminals including:

a pair of opposing electrode plates fixed together to clamp an end of said mesh heating element therebetween; and an elongated post extending from said plates for connection to a power source.

5. The in-line heater of claim 4 wherein each of the terminals further include:
a terminal sleeve seated in the terminal housing forming a bore in which the elongated post extends from the metal connector plates.

6. The in-line heater of claim 5 wherein:
each of said terminal sleeves has a serrated outer surface for mating engagement with said terminal housings of said tubular body.

7. The in-line heater of claim 1 wherein:
said tubular body is comprised of two longitudinally joined semi-cylindrical segments which form a substantially straight and unrestricted flow passage.

8. The in-line heater of claim 7 wherein:
said segments are hinged together along one longitudinal edge of each.

9. The in-line heater of claim 1 wherein:
said tubular body is a generally straight cylindrical tube.

10. The in-line heater of claim 1 wherein:
said tubular body is generally U-shaped.

11. The in-line heater of claim 9 including:
water trap means at the base of the U-shaped tubular body.

* * * * *